(12) United States Patent
Iddan (10) Patent No.: US 6,958,034 B2
(45) Date of Patent: Oct. 25, 2005

(54) SELF PROPELLED DEVICE

(75) Inventor: Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 22 days.

(21) Appl. No.: 10/361,855

(22) Filed: Feb. 11, 2003

(65) Prior Publication Data

US 2003/0214579 A1 Nov. 20, 2003

Related U.S. Application Data

(60) Provisional application No. 60/354,925, filed on Feb. 11, 2002.

(51) Int. Cl.$^7$ ................................. A61B 1/04
(52) U.S. Cl. ..................... 600/114; 600/109
(58) Field of Search .................. 600/109, 114

(56) References Cited

U.S. PATENT DOCUMENTS

| | | | |
|---|---|---|---|
| 3,322,374 A | 5/1967 | King, Jr. | |
| 3,683,389 A | 8/1972 | Hollis | |
| 3,971,362 A | 7/1976 | Pope et al. | |

(Continued)

FOREIGN PATENT DOCUMENTS

| | | |
|---|---|---|
| DE | 34 40 177 | 5/1986 |
| JP | 57-45833 | 3/1982 |
| JP | HEI 3-289779 | 12/1991 |
| JP | 4109927 | 4/1992 |
| JP | HEI 4-109927 | 4/1992 |
| JP | 4-144533 | 5/1992 |
| JP | HEI 4-180736 | 6/1992 |
| JP | 5015515 | 1/1993 |
| JP | 6114037 | 4/1994 |
| JP | 6285044 | 10/1994 |
| JP | 111985 | 5/1995 |
| JP | 7289504 | 11/1995 |
| JP | 2001137182 | 5/2001 |
| JP | 2001 224551 | 8/2001 |
| JP | 2001224553 | 8/2001 |
| WO | WO 92/21307 | 12/1992 |
| WO | WO 98/11816 | 3/1998 |
| WO | WO 99/30610 | 6/1999 |
| WO | WO 01/08548 | 2/2001 |
| WO | WO 01/50941 | 7/2001 |
| WO | WO 01/65995 | 9/2001 |
| WO | WO 02/067593 | 8/2002 |
| WO | WO 02/080753 | 10/2002 |

OTHER PUBLICATIONS

The Radio Pill, Rowlands, et al., British Communications and Electronics, Aug. 1960, pp. 598–601.
Video Camera to "TAKE"—RF System Lab, Dec. 25, 2001.
Wellesley company sends body monitors into space—Crum, Apr. 1998.
U.S. Appl. No. 10/361,861, filed Feb. 11, 2003, Iddan.
www.rfnorkia.com—NORIKA3, Dec. 24, 2001.
Wireless transmission of a color television moving image from the stomach using a miniature CCD camera, light source and microwave transmitter. Swain CP, Gong F, Mills TN. Gastrointest Endosc 1997;45:AB40.
BBC News Online—Pill camera to 'broadcast from the gut', Feb. 21, 2000, www.news.bbc.co.uk.
www.rfsystemlab.com—Listing on the N.Y stock exchange, downloaded Dec. 19, 2001.

(Continued)

*Primary Examiner*—Beverly M. Flanagan
(74) *Attorney, Agent, or Firm*—Pearl Cohen Zedek Laizer, LLP (57) ABSTRACT

A sensing device includes a propulsion system that is typically substantially or completely within the sensing device. The propulsion system may include, for example, a rotatable propeller. The sensing device may be an in-vivo autonomous capsule with an imager, but may be another type of sensing device.

22 Claims, 7 Drawing Sheets

U.S. PATENT DOCUMENTS

| | | | |
|---|---|---|---|
| 4,278,077 | A | 7/1981 | Mizumoto |
| 4,689,621 | A | 8/1987 | Kleinberg |
| 4,741,327 | A | 5/1988 | Yabe |
| 4,844,076 | A | 7/1989 | Lesho et al. |
| 5,279,607 | A | 1/1994 | Schentag et al. |
| 5,398,670 | A | 3/1995 | Ortiz et al. |
| 5,604,531 | A | 2/1997 | Iddan et al. |
| 5,643,175 | A | 7/1997 | Adair |
| 5,662,587 | A | 9/1997 | Grundfest et al. |
| 5,819,736 | A | 10/1998 | Avny et al. |
| 6,240,312 | B1 | 5/2001 | Alfano et al. |
| 6,632,175 | B1 | 10/2003 | Marshall |
| 6,702,734 | B2 * | 3/2004 | Kim et al. .................. 600/114 |
| 2001/0017649 | A1 | 8/2001 | Yaron |
| 2001/0051766 | A1 | 12/2001 | Gazdzinski |
| 2002/0103417 | A1 | 8/2002 | Gazdzinski |
| 2002/0173718 | A1 | 11/2002 | Frisch et al. |
| 2002/0198439 | A1 | 12/2002 | Mizuno |
| 2003/0018280 | A1 | 1/2003 | Lewkowicz et al. |
| 2003/0171648 | A1 | 9/2003 | Yokoi et al. |
| 2003/0171649 | A1 | 9/2003 | Yokoi et al. |
| 2003/0171652 | A1 | 9/2003 | Yokoi et al. |
| 2003/0214580 | A1 | 11/2003 | Iddan |
| 2003/0216622 | A1 | 11/2003 | Meron et al. |
| 2004/0027459 | A1 | 2/2004 | Segawa et al. |

OTHER PUBLICATIONS

U.S. Appl. No. 10/166,025, filed Jun. 11, 2002, Lewkowicz et al.

U.S. Appl. No. 10/213,345, filed Aug. 7, 2002, Glukhovsky.

Wang, et al., "Integrated Micro–Instrumentation for Dynamic Monitoring of the Gastro–Intestinal Tract", Presented at IEEE Instrumentation and Measurement Technology Conference, May 2002, Anchorage, Ak, USA, www.see.ed.ac.uk/Naa.publications.html.

Robots for the future—Shin–ichi, et al., downloaded Nov. 29, 2001.

* cited by examiner

SELF PROPELLED DEVICE

The present application claims benefit from prior provisional patent application Ser. No. 60/354,925 filed on Feb. 11, 2002 and entitled "SELF PROPELLED DEVICE", incorporated herein by reference in its entirety.

FIELD OF THE INVENTION

The present invention relates generally to self propelled devices, for example, for medical and other applications.

BACKGROUND OF THE INVENTION

Devices and methods for performing in-vivo imaging of passages or cavities within a body are known in the art. Such devices may include, inter alia, various endoscopic imaging systems and devices for performing imaging in various internal body cavities. Devices are also known for collecting other in-vivo data, such as temperature or pressure.

Typical in-vivo sensing systems are passive and are passively moved within the gastrointestinal (GI) tract by gravitation and by the peristaltic action.

There is suggested in the art a remote controlled microscale device for use in in vivo medical diagnosis and/or treatment, which includes a transport capsule containing a propulsion system.

Among the disadvantages of the devices known in the art is that any parts such as propellers, or the like, which protrude out of the rounded form of the medical device during the passage of the device through the intestines or other body cavity may increase the probability of puncturing or wounding or otherwise damaging or irritating the intestinal wall, or the walls of the bodily cavity in which the device is disposed.

Therefore there is a need for a device such as an in-vivo device which includes an improved propulsion system, one less likely to cause damage to a lumen being traversed.

SUMMARY OF THE INVENTION

Embodiments of the system and method of the present invention include a sensing device which includes a propulsion system that is typically substantially or completely within the sensing device. The propulsion system may include, for example, a rotatable propeller. The sensing device may be an in-vivo autonomous capsule with an imager, but may be another type of sensing device. A separate propulsion system may be provided which may be attachable to, for example, a sensing device.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

U.S. Pat. No. 5,604,531 to Iddan et al. and International Patent application PCT/IL01/00218, published as International Publication Number WO 01/65995, both incorporated herein by reference in their entirety for all purposes, disclose various embodiments of autonomous imaging devices usable, inter alia, for gastrointestinal imaging. Various embodiments of the present invention may be used with or incorporated within devices such as those described in U.S. Pat. No. 5,604,531 and/or PCT/IL01/00218; however, embodiments of the present invention may be used with or incorporated within devices having other structures and having other functions.

Figure 1A:
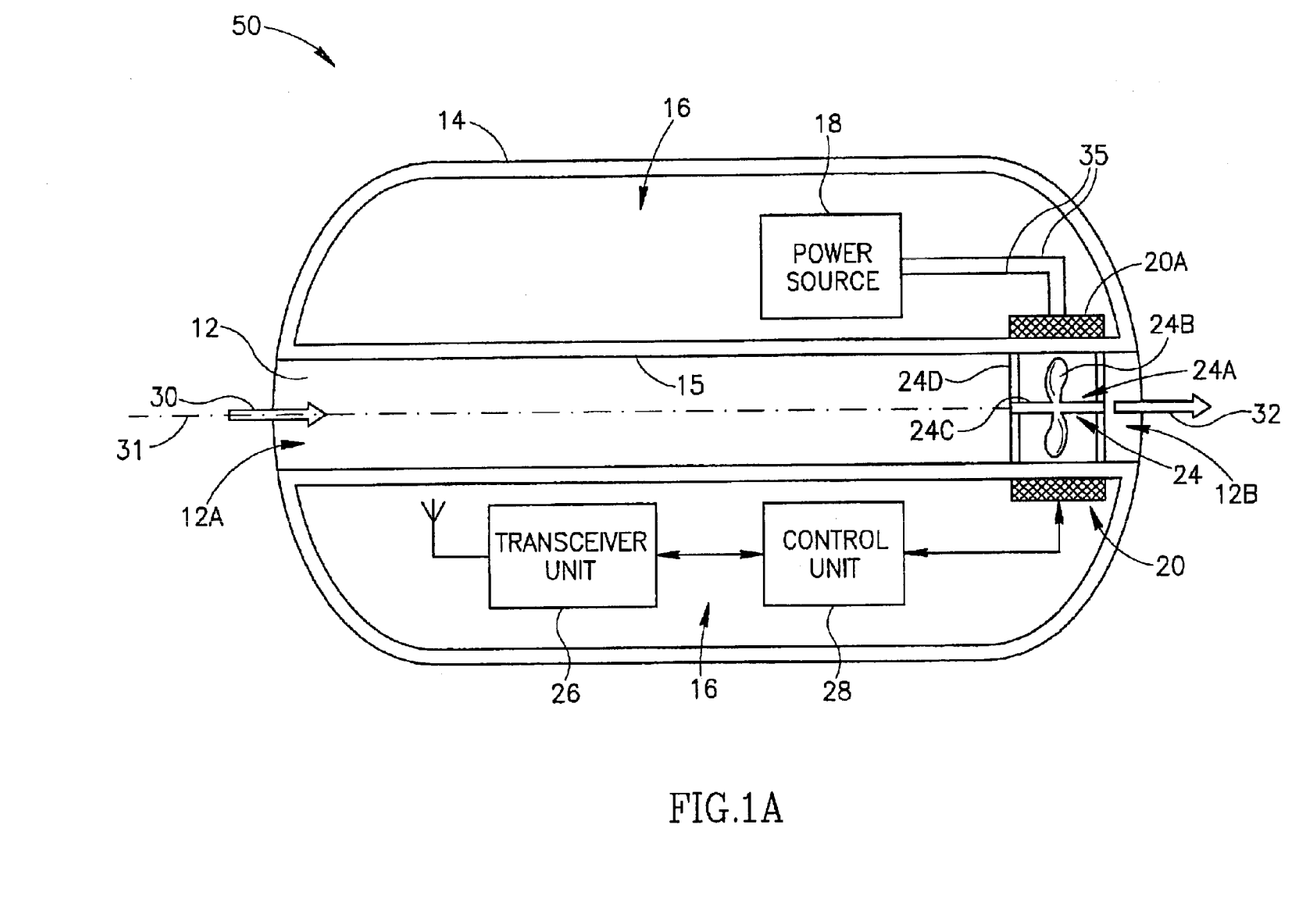
FIG. 1A is a schematic cross-sectional view illustrating a transport device having self propelling capability based on an ejected jet of fluid, using a non-protruding propelling system, in accordance with an embodiment of the present invention.

Reference is now made to FIG. 1A which is a schematic cross-sectional view illustrating part of a capsule-like transport device having self propelling capability based on an ejected jet of fluid, using a non-protruding propelling system, in accordance with an embodiment of the present invention.

Referring to FIG. 1A, the transport device 50 may have a body shaped as a capsule or elongated member. Such a capsule is typically autonomous and may be ingestible. In alternate embodiments, other shapes or configurations may be used, such as a sphere, ellipse, or other shapes. One or more hollow duct(s) 12 pass through the device 50, typically through the length of the device 50. The duct(s) 12 is typically surrounded by duct walls 15. The duct 12 has an opening 12A at a first end thereof and an opening 12B at a second end thereof. Other numbers of openings may be used. For example, either or both of openings 12A or 12B may be several openings. The duct 12 typically accepts fluid and expels the fluid outward, propelling the device 50.

The walls 14 of the transport device 50 typically enclose an internal space or volume 16 within which various different components (not shown) suitable for performing diagnostic, and/or imaging, and/or therapeutic functions, and/or controlling functions, and/or communication functions may be disposed. Typically, volume 16 is separate from duct(s) 12. Walls 14 and other structures may define the body or structure of device 50.

The transport device 50 typically is a general type of transport device and may be used to transport various different such components therewithin. The transport device 50 includes a motor 20. The motor 20 typically includes a stator unit 20A and a rotor unit 24. The rotor unit 24 is disposed within the duct 12 and the stator unit 20A is disposed within the volume 16. The rotor unit 24 may include a propulsion device such as a rotatable propeller unit 24A. The rotatable propeller unit 24A may include blades 24B attached to a rotatable axle 24C. The rotatable propeller unit 24A may be rotatably disposed within a mounting bracket 24D disposed within the duct 12 and attached to the walls 15 of the duct 12 of the transport device 50. The mounting bracket 24D is preferably configured as a hollow bracket such that it does not block the flow of fluid through the hollow duct 12. In a typical embodiment, the propeller or propulsion device is substantially or entirely within the device. Thus it is less likely that a moving part will come in contact with, for example, a lumen wall.

In accordance with one embodiment of the present invention, the rotor unit 24 is a permanently magnetized rotor unit. For example, in accordance with one embodiment of the present invention, the blades 24B of the rotatable propeller unit 24A may be magnetized blades. For example, the rotatable propeller unit 24A may include two (or other numbers) of typically opposed blades 24B which may be wholly or partially made from a permanently magnetized material such as but not limited to a neodymium-iron boron (Nd—Fe—B) alloy, or any other suitable permanently magnetized material known in the art. In such a configuration the blades 24B may together form a magnet such that one of the blades 24B is the north pole of the magnet and the other opposite blade 24B is the south pole of the magnet.

Figure 2:
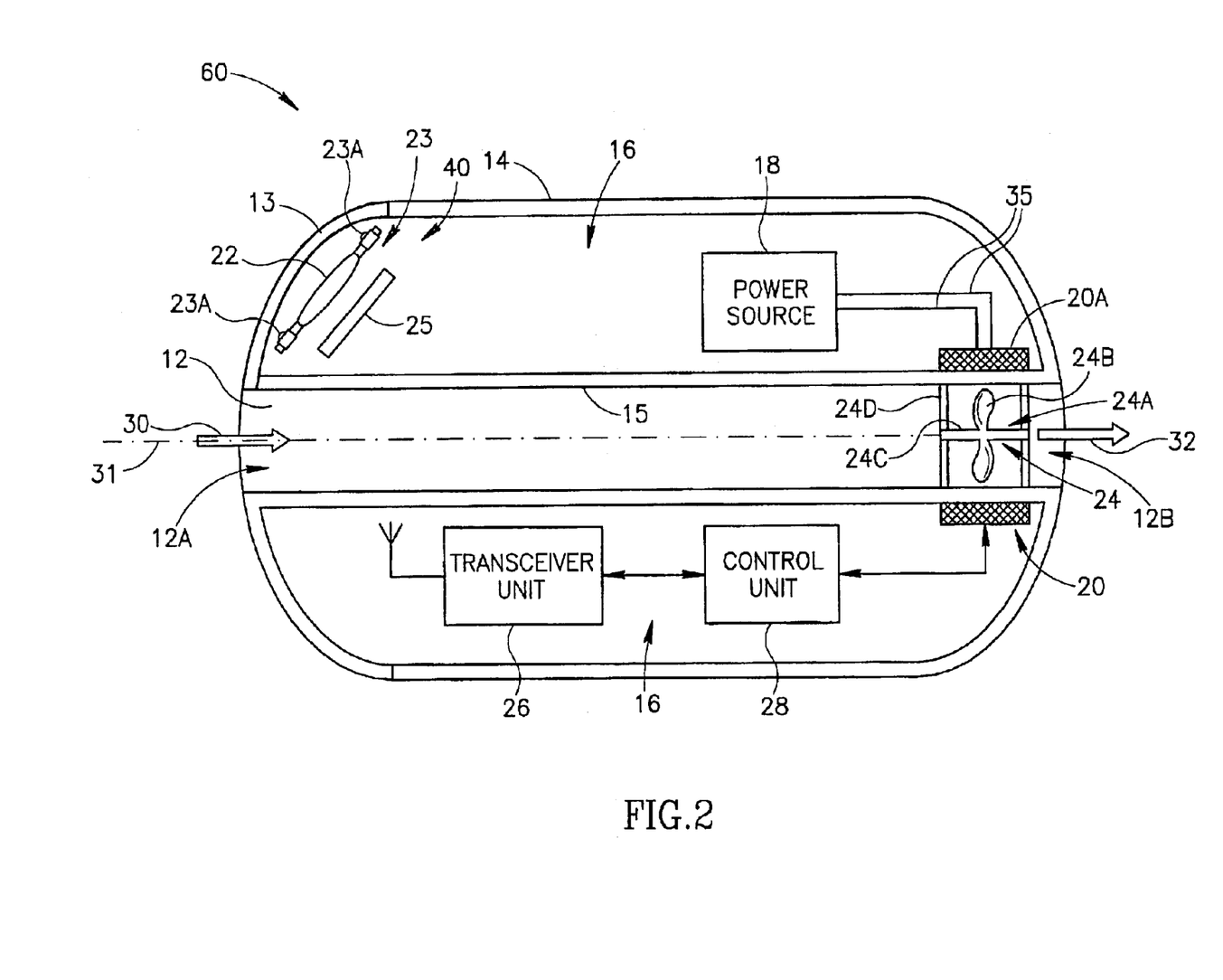
FIG. 2 is a schematic cross-sectional view illustrating an exemplary self propelling imaging device including an imaging system, in accordance with an embodiment of the present invention.

Alternatively, in accordance with another embodiment of the present invention, the rotatable axle 24C may be a magnetic axle, which may be permanently magnetized such that the direction of magnetization of the axle 24C is perpendicular to the longitudinal axis 31 (which coincides with the longitudinal axis of the axle 24C of FIG. 2).

The advantage of both of the configurations of the rotor unit 24A disclosed hereinabove is that the rotatable propeller unit 24A serves both as the rotor of the motor unit 20 and as the pumping element for propelling the fluid within the duct 12. Thus, in these embodiments there is no need for coupling of a separate rotor to a separate propeller unit, with the resulting simplification in construction and operation of the stator unit 20A.

In the embodiments in which the rotor unit 24 is a permanently magnetized rotor, the stator unit 20A may be an electromagnetic stator unit, as is known in the art. For example, the stator unit 20A may include one or more electrically conducting coils (not shown in detail), as is known in the art. The conducting coil(s) of the stator unit 20A may or may not include one or more coil cores (not shown) or may be wound on a suitable stator armature (not shown), as is known in the art.

In other embodiments, other types of motors or power providing systems may be used, and other propulsion devices may be used. For example, a propulsion device including a centripetal device, or other type of impeller may be used.

The device 50 may also include a power source 18 which may be disposed within the volume 16. The power source 18 may be suitably connected to the motor 20 by suitable electrical conductors 35 for providing power to the motor 20.

The power source 18 may be any suitable power source for providing power to the motor 20. For example, the power source 18 may be but is not limited to, one or more batteries, rechargeable batteries, electrochemical cells, fuel cells, or any other suitable electrical power source. The power source 18 may also be a power generating unit such as any device suitable for wirelessly receiving power from an external source and for providing electrical power to the motor 20. It is noted that in the cases where the power source 18 is a power generating unit for receiving energy from an external source, the power source 18 may include therein, or may be connected to a suitable power storage unit (not shown) for storing the generated energy. The power storage unit (not shown) may be any suitable storage unit, such as a rechargeable battery, or a super-capacitor storage unit, or the like, as is known in the art.

Published International Application number PCT/IL02/00283, publication number WO02/080753, assigned to the common assignee of the present application and incorporated by reference herein in its entirety, discloses methods and systems for transmitting power to an internal device; such methods may be used with embodiments of the present invention. For example, in various embodiments of the present invention, power may be received by the device 50 using, for example, a magnetic field. An energy receiving unit in the device 50 may include a coil configured to receive electromagnetic energy and an element, coupled to the coil, configured for converting the received electromagnetic energy to energy for powering the components of the device. The energy receiving unit may further be configured for storing the voltage, such as by including a capacitor or chargeable battery.

Thus, the power source 18 may also be a device adapted to wirelessly receive energy from an external energy source (not shown), such as, for example by receiving electromagnetic waves from an external transmitter and converting and storing electrical energy for use by the motor 20 or by any other devices (not shown) or components (not shown) included within the transporting device 50.

The power source 18 may receive power from external ultrasonic power sources (not shown), or electromagnetic wave sources (not shown), or magnetic sources (not shown), as is known in the art. The structure and operation of such power sources is well known in the art and is therefore not disclosed in detail hereinafter.

The device 50 may further include a control unit 28 suitably connected to the motor 20 for controlling the operation of the motor 20. The control unit 28 may be any suitable type of control unit known in the art. Preferably, the control unit 28 may be a micro-controller or microprocessor, as is known in the art, but other types of analog, or digital, or analog/digital hybrid control units may be used. The control unit 28 may include a wireless transceiver and/or transmitter unit 26, for communicating with an external transmitter and/or receiver unit (described below), and for receiving data and/or control commands from the external transmitter or transceiver. In one embodiment, the control unit 28 or its functionality may be part of or integrated with the transmitter and/or transceiver 26.

In operation, the device 50 may be immersed in a fluid or liquid (not shown). For example, in GI application the device 50 may be immersed in the fluids present in the GI tract. When power is supplied to the motor 20 with a certain polarity, the rotatable propeller unit 24A rotates in a first rotation direction and propels some of the fluid (not shown) in which the device 50 is immersed through the opening 12A in the general direction indicated by the arrow 30. The fluid may then be propelled through the length of the duct 12. The fluid may then be forcibly ejected out from the opening 12B as a fluid jet (not shown) in the general direction indicated by the arrow 32. The ejecting of the fluid jet through the opening 12B in the direction of the arrow 32 causes a movement of the device 50 in the direction opposite the direction of the arrow 32.

It is noted that the direction in which the device 50 is propelled may be changed by, for example, reversing the polarity of the electrical voltage difference supplied to the motor 20 by the power source 18. In such a case, the fluid jet will be ejected from the opening 12A and the device 50 may be propelled in the general direction of the arrow 32.

Such reversing may be controllably performed by the control unit 28 upon receiving (e.g., wirelessly or by wire) an appropriate control command or by any suitable internal logic command.

Figure 1B:
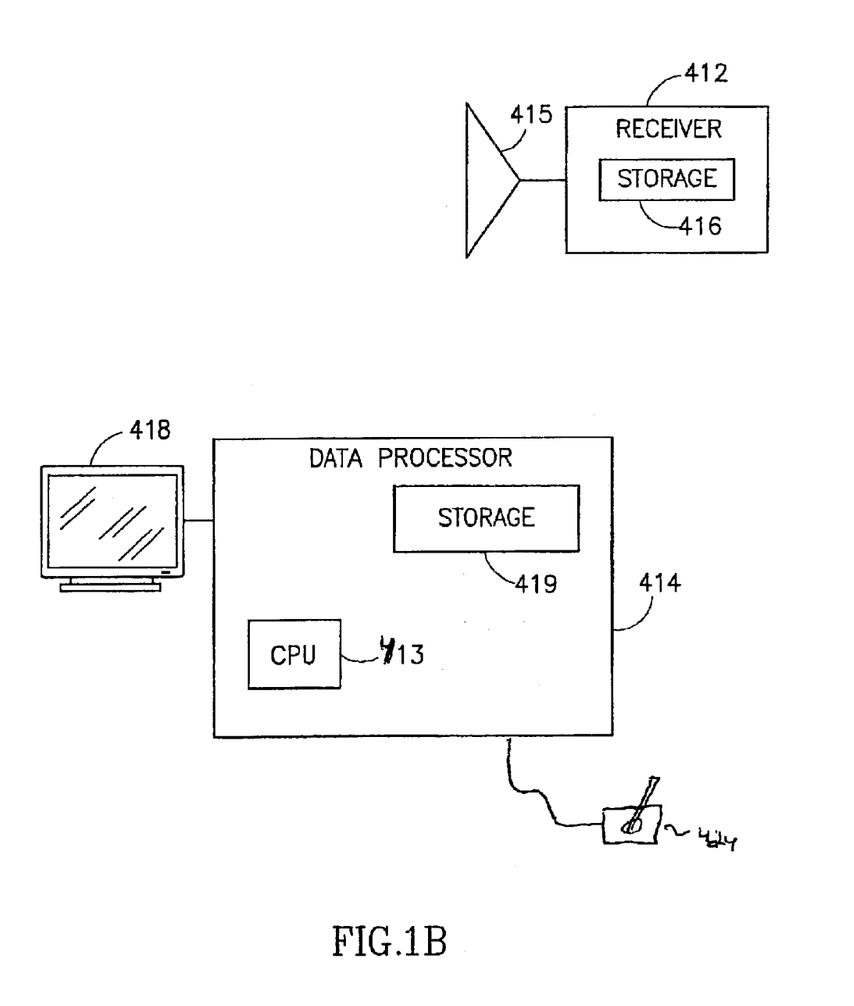
FIG. 1B is a schematic diagram of an external transmitter and/or receiver system and processing system, in accordance with an embodiment of the present invention.

FIG. 1B is a schematic diagram of an external transmitter and/or receiver system and processing system, in accordance with an embodiment of the present invention. Referring to FIG. 1B, preferably, located outside the patient's body in one or more locations, are a transceiver and/or receiver unit 412, preferably including an antenna or antenna array 415, for transmitting data to and/or receiving data from device 50 (FIG. 1A), a receiver storage unit 416, for storing data, a data processor 414, a data processor storage unit 419, and an image monitor 418. In some embodiments image monitor 418 may, for example, display, inter alia, data such as temperature or an image or representation of an in-vivo lumen, transmitted by the device 50 and recorded by the transceiver and/or receiver unit 412. The transceiver and/or receiver unit 412 may, for example, transmit control information or power to the device 50, and may receive image information, location information, temperature information, or other sensor information.

Typically, the transceiver and/or receiver unit 412 and receiver storage unit 416 are small and portable, and are worn on the patient's body during recording of the data. Preferably, data processor 414, data processor storage unit 419 and monitor 418 are part of a personal computer or workstation, which includes standard components such as a processor 413, a memory (e.g., storage 419, or other memory), software, a disk drive, and input-output devices, although alternate configurations are possible. A user control or input system such as a joystick or handle 424, for controlling the movement of the device 50, may be included. Other movement controls may be included, such as a keyboard, rotating knob, etc, may be used.

In alternate embodiments, the data reception and storage components may be of another configuration. For example, a portable recorder separate from a main workstation or data processor need not be used.

The receiving, recording and processing components may be, for example, similar to embodiments described in U.S. Pat. No. 5,604,531 and/or WO 01/65995. However, the receiving and recording components may be of other configurations.

Reference is now made to FIG. 2 which is a schematic cross-sectional view illustrating an exemplary self propelling imaging device including an imaging system attached, for example, within the transport device of FIG. 1A, in accordance with an embodiment of the present invention.

The imaging device 60 includes the transport device 50 of FIG. 1A and a sensor sensing system such as an imaging system 40. Other sensors or sensing systems, such as an ultrasonic sensing system, a pressure sensing system, etc., may be used. The imaging system 40 includes an optical system 22 and an imaging camera 25 (e.g., a CMOS camera, a CCD camera, or another type of imager) and an illumination unit 23 including one or more light sources 23A. The optical system 22, the imaging camera 25 and the illumination unit 23 may be constructed and operated as disclosed in detail for the optical system, the imaging camera and the illumination source of U.S. Pat. No. 5,604,531 and/or International Publication Number WO 01/65995. Alternately, such components may operate in accordance with other imaging systems.

The illumination unit 23 may illuminate a target to be imaged (target not shown) on the outside of the device 60 by illuminating the target through an optical window 13 with white light, or infra-red light, or other broadband or narrow-band light, including but not limited to laser light, coherent light, and incoherent light, or any suitable combinations thereof. The optical window 13 may be made from a material which is transparent to at least some of the wavelengths of light generated by the illumination unit 23 (such as a transparent plastic material, glass, quartz, or the like). An image of the target (not shown) is focused on the imaging camera 25 by the optical system 22. The illumination unit 23 and the imaging camera 25 are suitably connected to the power source 18 for receiving power therefrom (the connections between the illumination unit 23 and the imaging camera 25 and the power source 18 are not shown for the sake of clarity of illustration). The imaging system 40 is suitably connected to the control unit 28 (the connections between the imaging system 40 and the control unit 28 are not shown for the sake of clarity of illustration).

The control unit 28 may control the operation of the imaging system 40, the illumination unit 23, and the imaging camera 25. In accordance with one embodiment of the present invention, the control unit 28 may be part of or integrated within the imaging camera 25. In another embodiment, the control unit 28 or its functionality may be part of or integrated with a transmitter and/or transceiver.

The control unit may also control the operation and the transmitting and/or (optionally) the receiving of image data and/or command data from an external transceiver or receiver unit, as disclosed in detail in U.S. Pat. No. 5,604,531 and/or International Publication Number WO 01/65995. For example, the external receiver/transceiver and/or control system described in FIG. 1B may be used.

It is noted that the imaging system 40 may be inclined at an angle to the longitudinal axis 31 of the device 60 as illustrated in FIG. 2. In such a case of a tilted imaging system 40, the target which is imaged is disposed at an angle to the axis 31. It is noted, however, that this tilting is not mandatory and many other optical arrangements are possible, including but not limited to optical arrangements in which the optical system 40 is not inclined at an angle to the axis 31.

It is also noted that while the device 60 includes one imaging system 40, other embodiments of the device of the present invention may include more than one imaging system. In embodiments in which the device includes multiple imaging systems, each imaging system may provide a different image or the imaging systems may provide images which may be at least partially overlapping. Additionally, in devices having multiple imaging systems, different imaging systems may use different light sources to produce images at different spectral ranges (e.g. images of the same or different targets, using different wavelength ranges). Alternatively, different imaging systems (if used within a single imaging device) may use one or more common light sources, but may acquire images at different wavelength ranges by using appropriate filters (not shown), or by using different imagers having different spectral sensitivities.

Figure 3:
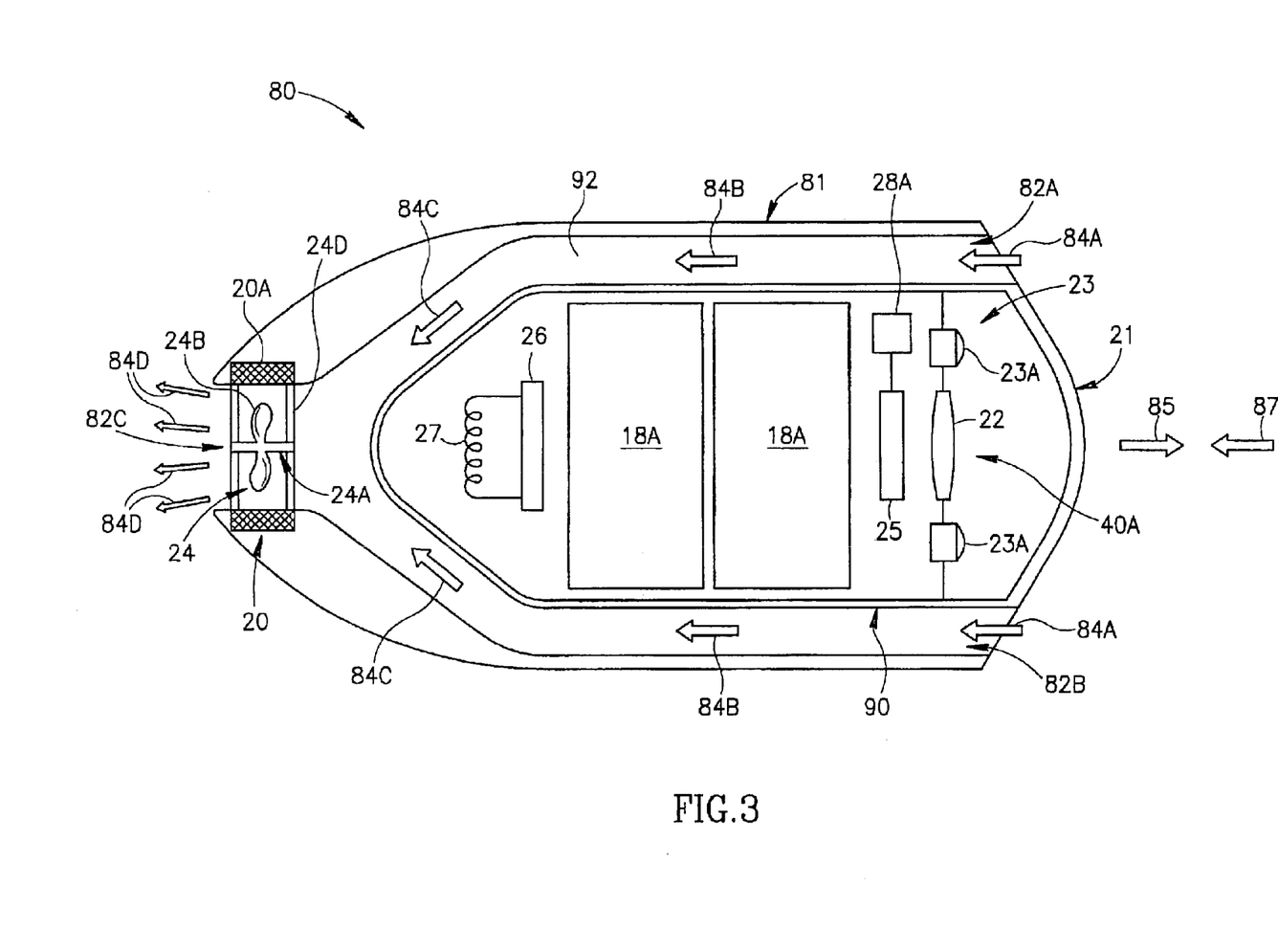
FIG. 3 is a schematic cross-sectional view illustrating an imaging device having self propelling capability based on an ejected jet of fluid in accordance with an embodiment of the present invention.
Figure 4:
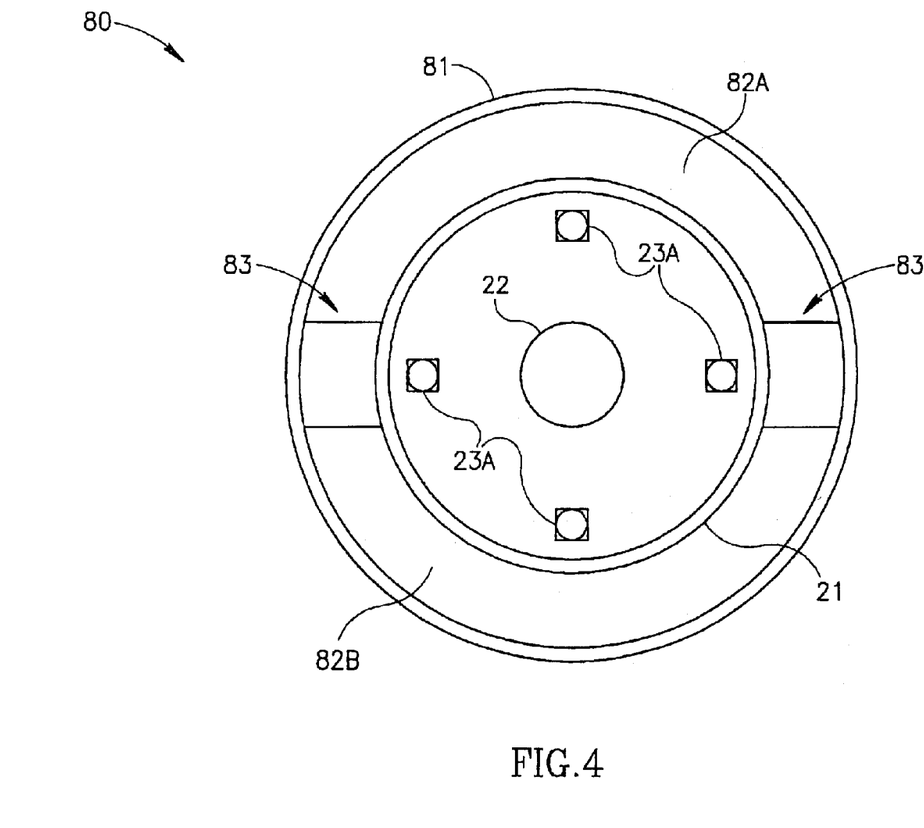
FIG. 4 is a schematic front view of the device illustrated in FIG. 3, according to an embodiment of the present invention.

Reference is now made to FIGS. 3 and 4. FIG. 3 is a schematic cross-sectional view illustrating an imaging device having self propelling capability based on an ejected jet of fluid in accordance with another embodiment of the present invention. FIG. 4 is a schematic front view of the device 80 of FIG. 3, according to one embodiment of the present invention. The front view of FIG. 4 illustrates the device 80 as seen from the direction represented by the arrow 87.

The device 80 of FIGS. 3 and 4 includes an external housing 81 and an internal housing 90. The internal housing 90 is disposed within the external housing 81 and is attached thereto by, for example, attaching members 83. The external housing 81 and the internal housing 90 define one or more hollow ducts 92 therebetween. The duct(s) 92 has openings 82A and 82B at one end thereof and an opening 82C at another end thereof. Other numbers of openings may be used. The duct 92 is typically within or substantially within the device, but need not be. Furthermore, the openings may be placed in other locations, and have other patterns of placement.

The device 80 includes a motor 20. The motor 20 typically includes a stator unit 20A and a rotor unit 24. The rotor unit 24 is typically disposed within the duct 92 and the stator unit 20A is disposed within the external housing 81. The rotor unit 24 may include a rotatable propeller unit 24A. The rotatable propeller unit 24A may include blades 24B attached to a rotatable axle 24C. The rotatable propeller unit 24A may be rotatably disposed within a mounting bracket 24D disposed within the duct 92 and attached to the walls of the external housing 81 of the device 80. The motor or power system may be of other structures, and have other components.

The device 80 typically includes a power source such as one or more batteries (or electrochemical cells) 18A which are disposed within the internal housing 90. The battery(ies) 18A are suitably connected to the motor 20 by suitable electrically isolated electrical conductors (not shown for the sake of clarity of illustration) for providing power to the motor 20. Other power sources may be used.

The imaging device 80 typically includes an imaging system 40A disposed within the internal housing 90. The imaging system 40A includes an optical system 22 and an imaging camera 25 (e.g., a CMOS camera, a CCD camera, or another type of camera) and an illumination unit 23. The optical system 22, the imaging camera 25 and the illumination unit 23 (which includes one or more light sources 23A), may be similar to those of U.S. Pat. No. 5,604,531 and/or International Publication Number WO 01/65995; however, other imaging systems may be used. The light sources 23A may be white light sources, or infra-red (IR) light sources, or other broadband or narrow-band light sources, including but not limited to laser light sources, coherent light sources, and incoherent light sources, or any suitable combinations thereof. Preferably, the light sources 23A are light emitting diodes (LEDs), but any other suitable light sources known in the art may be used.

The illumination unit 23 illuminates a target to be imaged (target not shown) on the outside of the device 80 by illuminating the target through an optical window 21. The optical window 21 may be made from a material which is transparent to at least some of the wavelengths of light generated by the illumination unit 23 (such as a transparent plastic material, glass, quartz, or the like). An image of the target is focused on the imaging camera 25 by the optical system 22. The illumination unit 23 and the imaging camera 25 are suitably connected to the batteries 18A for receiving power therefrom (the connections between the illumination unit 23 and the imaging camera 25, and the batteries 18A are not shown for the sake of clarity of illustration). The imaging system 40A is suitably connected to a control unit 28A which may control the operation of the imaging system 40A.

The control unit 28A may control the operation of the imaging system 40A, the illumination unit 23, and the imaging camera 25. In accordance with one embodiment of the present invention, the control unit 28A may be part of or integrated within the imaging camera 25. In another embodiment, the control unit 28A or its functionality may be part of or integrated with the transmitter and/or transceiver 26.

The control unit 28A may be suitably connected to the motor 20 for controlling the operation of the motor 20. The control unit 28A may be any suitable type of control unit known in the art. The control unit 28A may be a microcontroller or microprocessor, as is known in the art, but other types of analog, or digital, or analog/digital hybrid control units may be used. The control unit 28A may also be an integral part of the imaging camera 25, as disclosed hereinabove.

The device 80 may also include a wireless transceiver and/or transmitter 26, for communicating with an external transmitter and/or receiver unit (such as described above), and for receiving data and/or control commands from the external transmitter or transceiver. The transceiver unit 26 may be connected to a suitable antenna 27. In one embodiment, the control unit 28 or its functionality may be part of or integrated with the transmitter or transceiver 26

In operation, the device 80 may be immersed in a fluid or liquid (not shown). For example, in gastrointestinal application the device 80 may be immersed in the fluids present in the gastrointestinal tract. When electrical power is supplied to the motor 20 with a certain polarity, the rotatable propeller unit 24A rotates in a first rotation direction and propels some of the fluid (not shown) in which the device 80 is immersed through the openings 82A and 82B in the general direction indicated by the arrows labeled 84A. The fluid may then be propelled through the duct 92 in the direction schematically represented by the arrows labeled 84B, and 84C. The fluid may then be forcibly ejected out from the opening 82C as a fluid jet (not shown) in the general direction indicated by the arrows labeled 84D. The ejecting of the fluid jet through the opening 82C in the direction of the arrows labeled 84D may cause a movement of the device 80 in the direction opposite the direction schematically represented by the arrow labeled 85.

It is noted that the direction in which the device 80 is propelled may be changed by reversing the polarity of the electrical current (or voltage) supplied to the motor 20 by the batteries 18A. In such a case, the fluid may be taken in through the opening 82C and the fluid jet will be ejected from the openings 82A and 82B, and the device 80 may be propelled in the general direction of the arrow labeled 87.

Such reversing may be controllably performed by the control unit 28A upon receiving (e.g., wirelessly or by wire) an appropriate control command.

It is noted that while the devices 50 and 60 (of FIGS. 1A and 2, respectively) have a single central duct 12 having a first opening 12A and a second opening 12B, and while the device 80 of FIGS. 3–4 has a partially circumferential duct 92 having two openings 82A and 82B and a third opening 82C, many other configurations of the ducts and openings may be used in various different embodiments of the present invention all of which are considered to be within the scope and spirit of the present invention.

For example, in accordance with other embodiments of the invention, any device of the devices 50, 60 and 80 may be modified or configured to include more than one duct. The use of a plurality of ducts may be advantageous since it may be possible to configure the ducts such that their openings may be oriented in different direction. This arrangement may enable the ejection of different fluid jets in different directions (either simultaneously or sequentially) which may improve the ability to control the direction of propelling of the device.

If a device according to an embodiment of the present invention includes a plurality of separate ducts, each duct may include a separate motor. Such separate motors may be suitably controlled by the control unit operating the device (such as, for example, the control unit 28 or 28A of FIGS. 1–2, and FIG. 3, respectively).

Alternatively, in accordance with another embodiment of the present invention, the device may include a common duct having a single motor disposed therewithin, such as but not limited to the motor 20 disclosed hereinabove. The common duct may have one or more openings for fluid intake, and secondary ducts branching off the common duct. Each of the secondary ducts may have a plurality of openings through which fluid may be ejected to provide a propulsive force or forces. Some or all of the secondary ducts and the openings thereof may be configured such that they are capable of ejecting fluid jets oriented at various different directions relative to the longitudinal axis of the device.

One or more of the secondary ducts may have controllable valves disposed therein and suitably connected to a control unit (such as, but not limited to, the control units 28, and 28A) to control the ejection of the fluid jets through the opening(s) of the secondary ducts. This arrangement may be advantageous since it may provide a more flexible propulsion capability and may be capable of controllably propelling the device in different directions by selectively opening and closing various combinations of valves. Another advantage of this embodiment is that a single motor may be used while still enabling the control of device propulsion through controlling of appropriately selected valves. Other components may be used to aid in directing the device. For example, baffles or vanes may alter, increase, decrease or direct the flow of fluid. Rudders may be used.

It is further noted that the control units 28 and 28A of the devices 50, 60 and 80 disclosed hereinabove may be used to control the parameters of the fluid jet ejection by controlling the speed of rotation of the rotor unit 24 of the motor 20, as well as the direction of rotation of the rotor unit 24 as disclosed hereinabove. Similar control of the speed and direction of the rotor unit may also be used in embodiments of the invention having multiple motors.

The use of multiple fluid jets having different orientations and velocity may be used to propel the device(s) in various different directions, and to provide not only forward or backward propulsion directions but also various rotational movements (such as for example, a rotation of the device around the longitudinal device axis), and may be used to rotate the device in different directions at an angle to the longitudinal axis of the device. Thus, in principle, most movement control methods known in the art for devices based on the ejection of a fluid, or a gas, or a liquid (such as, but not limited to, jet planes rockets, missiles, marine and submarine vehicle propulsion systems, and the like) may be adapted for use in the devices of the present invention.

It is noted that in accordance with other embodiments of the present invention, the devices of the present invention may include more than one motor. For example, devices including a single or multiple ducts may include a single motor as illustrated in FIGS. 1A and 4, but may also have multiple motors. These motors may be suitably disposed within suitable ducts in devices which have a plurality of ducts. Alternatively, in devices having a single duct or multiple ducts, more than one motor may be disposed in one duct.

In devices having a common duct with secondary ducts, one or more motors may be disposed within the common duct, or one or more motors may be disposed within some or all of the secondary ducts.

Moreover, while the embodiments disclosed hereinabove and illustrated in the drawings have a motor which has a single set of propellers (when used herein set can include one unit), in other embodiments of the present invention a motor may have multiple propellers therein, or other types of propulsion devices, such as centripetal devices, or other impellers. Furthermore, while the devices disclosed herein and illustrated in the drawings have two blades per rotor (such as the two blades 24B of the rotor unit 24 of FIG. 1A), many other rotor and blade configurations may be used, as is known in the art. For example, the rotor unit 24 may have more than two blades arranged in any suitable configuration (including various suitable mechanical and (optionally) magnetic configurations, where relevant).

It will be appreciated by those skilled in the art that the devices disclosed hereinabove and illustrated in FIGS. 1–4 are not limited to including only imaging systems. Many other types of different diagnostic, therapeutic, surgical, ultrasonic, and sampling devices may be included in the self propelling devices of embodiments of the present invention.

It is further noted that, while the devices of the present invention may include an imaging system therein, the imaging system is not an obligatory part of the self propelled devices of the present invention and many such self propelled devices with a non-protruding propulsion unit or propelling system may be constructed in accordance with embodiments of the present invention, which do not include an imaging system but which may include other sensing units or any suitable combination of therapeutic, and/or diagnostic, and/or surgical, and/or spectroscopic, and/or sampling, and/or ultrasonic, components known in the art.

Figure 5:
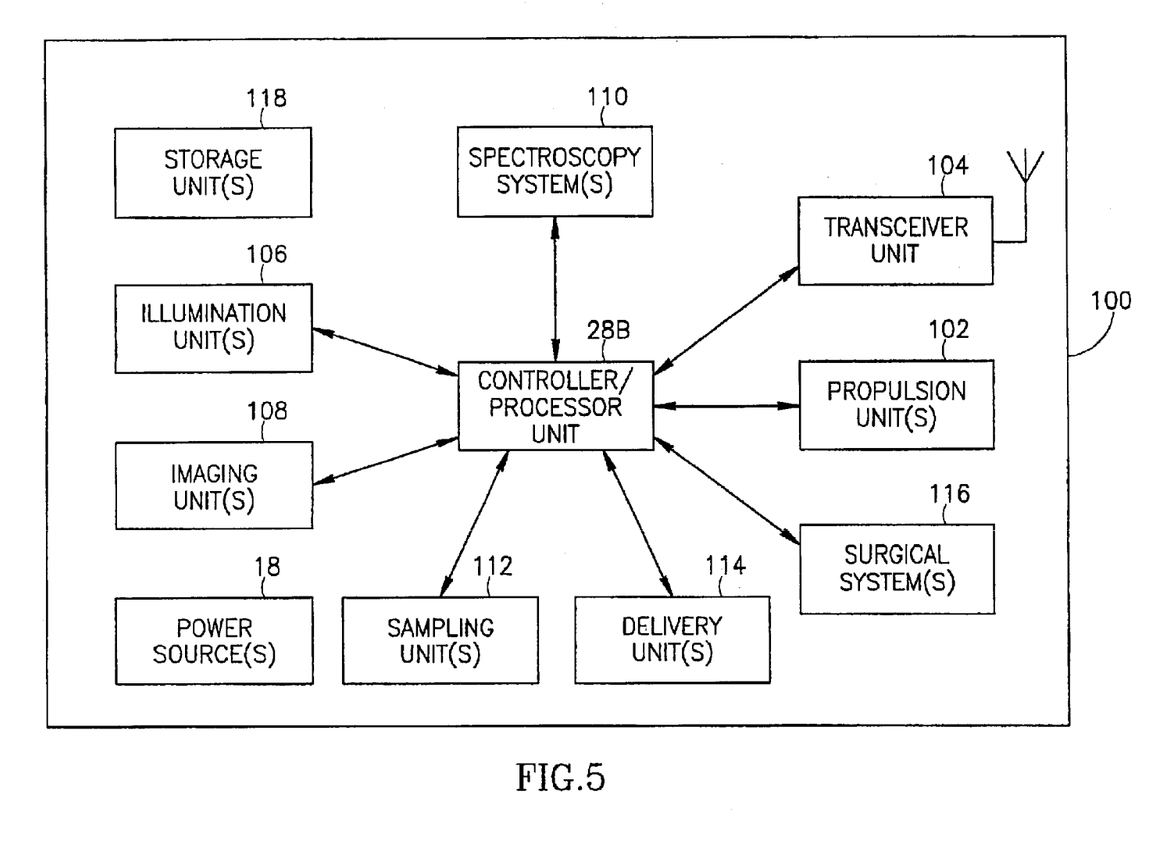
FIG. 5 is a schematic block diagram illustrating the components of an exemplary self propelling imaging/diagnostic/therapeutic device having a non-protruding propelling system, in accordance with an embodiment of the present invention.

Reference is now made to FIG. 5 which is a schematic functional block diagram illustrating the components of an exemplary self propelling imaging/diagnostic/therapeutic device having a non-protruding propelling system, in accordance with another embodiment of the present invention.

The device 100 typically includes a controller/processor unit 28B, one or more propulsion units 102, such as non-protruding or substantially non-protruding propulsion units, a transceiver unit 104, one or more illumination units 106, one or more imaging units 108, and one or more power source(s) 18. The controller/processor unit 28B is suitably connected to the propulsion unit(s) 102, the transceiver unit 104, the illumination unit(s) 106, and the imaging unit(s) 108, for controlling the operation thereof.

The device 100 may further include, for example, one or more spectroscopy units 110, one or more sampling units 112, one or more delivery units 114, and one or more surgical systems 116. Other functional systems or sensors may be included. The controller/processor unit 28B may be suitably connected to the spectroscopy unit(s) 110, the sampling unit(s) 112, the delivery unit(s) 114, and the surgical system(s) 116, for controlling the operation thereof.

The spectroscopy unit(s) 110 may be adapted for performing spectroscopic analysis of target tissues (in in vivo applications) or of target objects in other industrial applications, as is known in the art.

The sampling units 112 may be configured and adapted to collect samples of body fluids or to collect a biopsy sample (in in vivo applications) or to collect samples of other fluids in other industrial applications as is known in the art.

The delivery units 114 may be configured and adapted to deliver quantities of a substance or substances to a target body part or organ part or to a body lumen (in in vivo applications). The substance(s) which may be delivered may be a drug, a therapeutic substance or other medication, or a pharmaceutical composition. Preferably, the substance(s) may be delivered in a liquid form which is dispensed from the delivery unit(s) 114 which include a controllably openable storage vessel.

The delivery units 114 may be configured and adapted to deliver quantities of a substance or substances to a target site in other industrial applications, as is known in the art.

The surgical systems 116 may be adapted and configured to perform one or more of surgical procedures, including but not limited to perform a biopsy procedure (preferably, but not necessarily, under visual control), resection of a tumor or part thereof, surgical removal of intestinal or other polyps, or the like. Many other surgical procedures may be performed by the surgical systems 116, such as, laser ablation of target tissues, photo-dynamic therapy (PDT) procedures, which may or may not include the delivery of a suitable PDT dye from the delivery unit(s) 114, or any other suitable surgical procedure.

The details of construction and operation of the spectroscopy unit(s) 110, the sampling unit(s) 112, the delivery unit(s) 114, and the surgical system(s) 116, are known in the art, are not the subject matter of the present invention, and are therefore not described in detail hereinafter. Briefly, the spectroscopy unit(s) 110, the sampling unit(s) 112, the delivery unit(s) 114, and the surgical system(s) 116 may be constructed and operated as known in the art.

The power source 18 may be suitably connected (the connections are not shown for the sake of clarity of illustration) to the controller/processor unit 28B, the propulsion unit(s) 102, the transceiver unit 104, the illumination unit(s) 106, the imaging unit(s) 108, the spectroscopy unit(s) 110, the sampling unit(s) 112, the delivery unit(s) 114, and the surgical system(s) 116 for providing power thereto.

The controller/processor unit 28B may be suitably coupled to one or more storage units 118 for storing data, and/or commands, and/or program code therein. The storage unit(s) 118 may include one or more memory devices (not shown in detail), such as but not limited to random access memory (RAM) device(s), read only memory (ROM), programmable read only memory (PROM) device(s), electrically programmable read only memory (EPROM) device(s), erasable electrically programmable read only memory (EEPROM) device(s), flash memory (FEPROM) device(s), or the like, or any suitable combinations of memory devices known in the art. However, the storage unit(s) 118 may be any other suitable storage device or storage means known in the art and suitable for storing data or information, such as but not limited to magnetic storage device(s), magneto-optical storage device(s), optical storage device(s), holographic storage device(s), or the like.

It is noted that the spectroscopy unit(s) 110, the illumination unit(s) 106, the surgical systems(s) 116, may or may not include laser device(s) as is known in the art, and may or may not include other coherent or non-coherent light sources for illumination, and/or spectroscopy, and/or therapeutic purposes, depending on the specific configuration of the device 100. White light emitting diodes (LEDs) may be included for illuminating and/or spectroscopy purposes, as is known in the art. Other types of LEDs may be also included, such as but not limited to infra-red LEDs, and/or LEDs having a narrow or intermediate spectral bandwidth (such as but not limited to, red LEDs, green LEDs, blue LEDs, laser diodes, or the like. Other types of light sources known in the art may or may not be included in the device 100 depending on the application.

The controller/processor unit 28B may be any suitable type of control unit known in the art. The controller/processor unit 28B may be a micro-controller or microprocessor, as is known in the art, but other types of analog, or digital, or analog/digital hybrid control units may be used. The controller/processor unit 28B may also be an integral part of one of the imaging units 108, as disclosed hereinabove. Alternatively, the controller/processor unit 28B may be integrated into any other suitable electronic circuit or integrated circuit of the device 100.

It is noted that the connections between the control units 28 and other components included within the devices 50 and 60 are not shown in detail and are only illustrated schematically. The exact configuration of the connections between the control units 28 and these components depends on the specific implementation of the devices 50 and 60, are well known in the art, are not the subject matter of the present invention, and are therefore not disclosed in detail.

It is further noted that the connections between the control units 28A and other components included within the device 80 are not shown in detail and are only illustrated schematically. The exact configuration of the connections between the control units 28A and these components depends on the specific implementation of the device 80, are well known in the art, are not the subject matter of the present invention, and are therefore not disclosed in detail.

It is further yet noted that the connections between the control units 28B and other components included within the device 100 are not shown in detail and are only illustrated schematically. The exact configuration of the connections between the control units 28B and these components depends on the specific implementation of the device 100, are well known in the art, are not the subject matter of the present invention, and are therefore not disclosed in detail.

In one embodiment, a propulsion unit may be a separate unit, and may be capable of attachment or joinder to an in-vivo sensing device, or another type of sensing device. In one embodiment, no redesigning of an existing capsule or is other sensing device may be needed to add propulsion capability. Such a propulsion unit may be a stand alone unit with separate components, although in some embodiments some components (e.g., power source, controller etc.) may be shared via, for example, a link.

Figure 6:
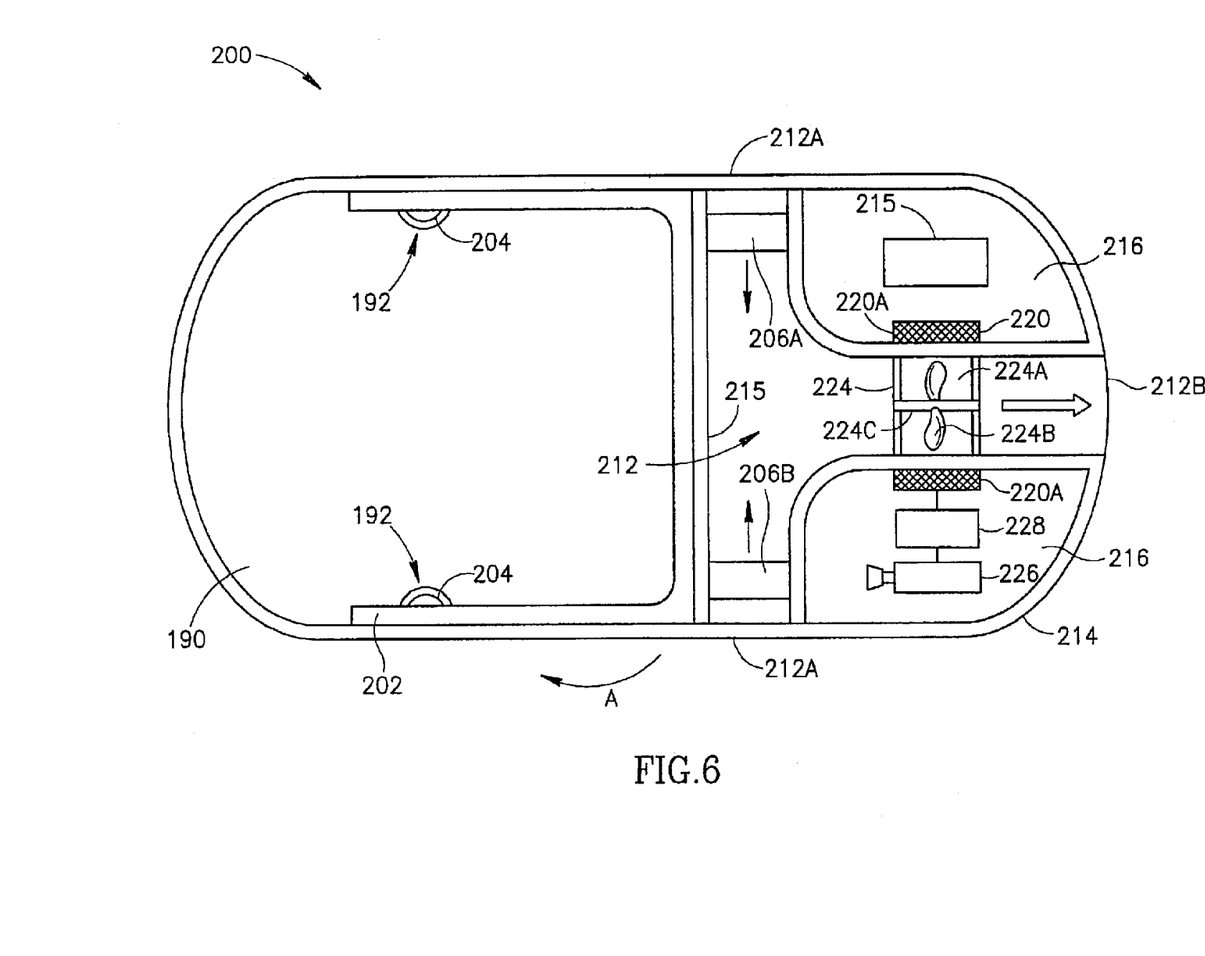
FIG. 6 depicts a propulsion unit connected to an in-vivo sensing device, according to one embodiment of the present invention.

FIG. 6 depicts a propulsion unit connected to an in-vivo sensing device, according to one embodiment of the present invention. Referring to FIG. 6, a propulsion device 200 is connected to an in-vivo sensing device 190. In vivo sensing device 190 may be any sort of in-vivo sensing device, such as those described in U.S. Pat. No. 5,604,531 and/or International Patent application PCT/IL01/00218; other in-vivo sensing devices may be used. In one embodiment, in-vivo sensing device 190 is an oblong capsule, but other shapes (e.g., sphere, ellipse, etc) may be used.

Typically, a connector or connection system such as friction fit sleeve 202 is used to connect propulsion device 200 to sensing device 190. In one embodiment, friction sleeve 202 holds and surrounds a portion of sensing device 190 to propulsion device 200. Sensing device 190 and propulsion device 200 may be separate, autonomous units, and may be connected by a user, at a factory, etc. Typically, when connected, sensing device 190 in combination with propulsion device 200 forms a swallowable shape and size, such as an appropriately sized capsule or sphere, but need not, depending on the application.

In one embodiment, other or additional connectors or connection mechanisms may be used, such as an optional dimple/recess mechanism, where one part, e.g., propulsion device 200, includes one or more dimples or protrusions 204, and another part, e.g. sensing device 190, includes one or more indentations or recesses 192. Other methods of attachment, such as a screw/thread system, etc., may be used.

The components of the propulsion device 200 may be similar in structure and function to those described in the various embodiments above. One or more hollow ducts 212 allow the passage of fluids through the body of the propulsion device 200, and include one or more inlets 212A and outlets 212B. The duct(s) 212 is surrounded by the duct walls 215. The walls 214 of the propulsion device 200 enclose one or more volume(s) 216. The walls 214 of the propulsion device 200 and duct walls 215 may be the same structures. Walls 215, walls 214 and/or other structures may define the body of the device 200.

The propulsion device 200 includes a motor 220. The motor 220 includes, for example, a stator unit 220A and a rotor unit 224. The rotor unit 224 is typically disposed within the duct 212 and the stator unit 220A is typically disposed within the volume(s) 216. The rotor unit 224 may include a propeller unit 224A, including, for example, blades 224B attached to a rotatable axle 224C. The rotatable propeller unit 224A may be rotatably disposed within a mounting bracket 224D, similar to that described above. The various components of the motor 220 may be similar to those described above, or may in other embodiments vary.

The propulsion device 200 may also include a power source 218, suitably connected to the motor 220. The power source 218 may be any suitable power source. The propulsion device 200 may include a control unit 228, e.g., a microcontroller or microprocessor, as described above, or another type of control unit. The control unit 228 may be connected to or may include wireless transceiver unit 226, for external communication, as described above.

In one embodiment, in operation, the motor 220 can be activated in a reverse direction, so that fluid flows through the ducts 212 in the opposite direction.

While in one embodiment two peripheral inlets 212A are shown, there can be a ring of any number of openings as well. The propeller unit 224A may be positioned other than in the central duct of the ducts 212; one or more propeller units may be in any one of the peripheral channels of the ducts 212. More than one propeller unit may be used.

In an embodiment where multiple inlets or multiple outlets are used, one or more valves such as selectively operable valves 206 may be used to aid in controlling the direction of movement of the propulsion device 200. Valves 206 may be one-way or two way, adjustable or not, and need not be used or included. For example, in the embodiment shown, the closure of valve 206A while the motor 220 is reversed may cause the capsule to rotate in the direction of arrow "A". In the embodiment shown, the closure of valve 206A while the motor 220 is in forward mode may cause the capsule to rotate in the opposite direction of arrow "A". In alternate embodiments, other arrangements of ports may be used. Further, selective flow control can be provided by, for example, more than one motor or propulsion unit.

In one embodiment, a self propelled device as described variously above may be steerable or may otherwise have its direction controlled. In addition, such a device may have its motion or position tracked. Position data may include location and/or orientation data. Position determining elements may be included within the device (e.g., magnetic coils, a transmitter or antenna) and/or may be external to the device. In one embodiment, a position unit or position determining elements can be part of the transmitter and/or antenna transmitting other data. Such movement or position information may aid in a user or an automatic system (e.g., an external software program, such as one operating under control of processor 414) in controlling or deciding to operate a propulsion system, or in controlling the direction of movement of such a device.

In one embodiment, location and possibly orientation information for a self-propelled device (such as the devices 50, 60, 80, 100, 190 and/or 200) are determined. Alternately (or in addition), movement information, such as whether or how much the device is moving over time, may be obtained. In one embodiment, motion information may be combined with location and/or orientation information—for example, motion information may provide fine movement determinations not relative to a reference frame. Such information may be used to guide the device, to determine if the device is stuck and needs aid from a propulsion device, or for other reasons. In alternate embodiments, such movement, location and/or orientation information need not be used.

In one embodiment, motion or movement detection may be provided, by, for example, an on-board accelerometer or other device. For example, structures and techniques for motion detection used in International Application No. PCT/IL98/00608, International Publication number WO 99/30610, assigned to the same assignee as the present application, and incorporated by reference in its entirety, may be used.

In a typical embodiment, location detection methods such as those discussed in United States patent application publication number US-2002-0173718-A1, filed May 20, 2002, entitled "Array System and Method For Locating an In-Vivo Signal Source," assigned to the assignee of the present invention, and incorporated herein by reference, may be used.

Other location and/or orientation detection methods may be used. In one embodiment, the orientation information includes three Euler angles or quaternion parameters; other orientation information may be used. Location and orientation information may be determined by, for example, including two or more transmitting antennas in the above devices, each with a different wavelength, or by detecting the location and orientation using a magnetic method. Methods such as those using ultrasound transceivers or monitors that include, for example, three magnetic coils that receive and transmit positional signals relative to an external constant magnetic field may be used. A GPS or GPS like system may be used; for example a system using transmission from 3 or more stations. If a phase and frequency is used which is high enough (e.g., 300 MHz), a resolution of 1 mm is possible. Other GPS or GPS like systems may be used.

In one embodiment, a transceiver within the device includes, for example, three electrodes, coils or transponders that receive signals (e.g., electromagnetic signals) transmitted from an external source. The external source includes, for example, three transmitters (e.g., electromagnetic transmitters) at a fixed position in an external reference frame that transmit, for example, three distinguishable electromagnetic radiations (such as at different frequencies). The electrodes, coils or transponders receive signals corresponding to the different electromagnetic radiations at a plurality of times, each of the signals including components of at least one of the different radiations. The position and the orientation of the device can be determined from the data received from electrodes, coils or transponders. The electrodes, coils or transponders form signals that include the components of the signal received by the each electrode from the three transmitters.

Calculations for determining the in vivo position and orientation of objects may be carried out on suitable computational or processing devices, for example using data processor 414 and the appropriate software. Such calculations may be any of those known methods described above. For example, data which may aid in location and/or orientation determination is transmitted via, for example, transceiver and/or transmitter unit 26 (described above), received by transceiver and/or receiver unit 412, and downloaded to data processor 414. Alternately, processing capability within the device can determine a position within the reference frame, and this position information may be transmitted via transceiver and/or transmitter unit 26 to be downloaded to data processor 414.

Of course, other location and/or orientation determining methods may be used.

In one embodiment, the data processor 414 displays on monitor 418 a location or path representation of the device. Since the monitor 418 is typically two dimensional, and the path of the device is typically three dimensional, the path representation may be two dimensional, or may be displayed using techniques that include three dimensional information to the two dimensional image. For example, shading or coloring may indicate three dimensional aspects; other techniques may be used. Orientation information may be included. Other methods for displaying location and/or orientation information may be used.

A user may, using a user control or input device (e.g., joystick or handle 424), input information to the data processor 414. The data processor 414 may convert such information into movement controls to be sent to the various components of the device (e.g. the motor, valves) via transceiver and/or receiver unit 412. For example, commands sent may cause the motor 220 to alter its speed or reverse its direction.

Self propulsion may be desirable for an in-vivo sensing device for various reasons. In one embodiment, where a device traverses the GI tract, propulsion may be desirable in voluminous lumens, such as the stomach or the colon. In the colon, for example, peristaltic motion may be substantially reduced, and thus the device may not be pushed through the colon in an acceptable time frame. The device may stay in the colon until there is bowel movement. The colon typically has a wavy wall structure, and a device may become stuck in one of the waves. Further, at the entrance to the colon (from the small bowel) in the cecum, a device may also get stuck. In addition, the path of an advancing device in the colon may work against gravity, due to the general "C" shape of the colon. In other applications, there may be similar or other reasons why self propulsion is desirable.

While the devices 50, 60, 80, 100, and 190 are particularly adapted for application as a device for performing imaging and/or therapy/surgery/diagnosis/procedures within the gastrointestinal tract or within any other body lumen (including but not limited to blood vessels, and the heart), other applications of the present invention may also include devices configured for use in other environment such as, but not limited to imaging and performing sampling, and/or analytical, and/or maintenance, and/or various treatment procedures in industrial or other environments, such as, for example, within vessels, tubes or pipelines in industrial equipment, or within buildings, or the like.

It will be appreciated by the person skilled in the art that many modifications and variations in the configuration and the type of motor unit used in embodiments of the present invention. For example, the motor may be configured and constructed in accordance with any suitable motor design known in the art, including but not limited to, direct current (DC) motors, alternating current (AC) motors, synchronous or asynchronous motors, motors having permanently magnetized rotors, motors having permanently magnetized stators, motors having electromagnetic rotors, motors having electromagnetic stators, or any combinations thereof.

It is noted that the embodiments of the motor disclosed hereinabove may typically (but not obligatorily) be of the brushless type which includes a permanently magnetized rotor. This type of motor typically includes one or more sensors which sense the position and/or the orientation of the rotor for controlling the operation of the stator. Such sensor(s) may form part of a brushless commutating circuit, or commutating device, as is known in the art. Such sensor(s) may be optical sensor(s), Hall effect sensor(s), or any other type of sensor known in the art. It is noted that the details of construction and operation of brushless motors and commutating circuits and devices is well known in the art and is therefore not disclosed in detail herein.

Moreover, any suitable types of motors or propulsion units known in the art, which are different than the motors shown may be used in the devices of the present invention in any of the non-protruding configurations disclosed hereinabove and illustrated in the drawings.

Furthermore, while the devices disclosed hereinabove and illustrated in the drawing figures are autonomous self propelling devices, the non-protruding propulsion system of the present invention may also be used and implemented in other endoscopic or other devices. Thus, in accordance with additional embodiments of the present invention, an endoscope-like device, or catheter-like device, or tethered capsule-like device may be adapted to include a non-protruding propulsion system in which a motor may be included within one or more non-protruding duct or cavity within the endoscope-like device, or catheter-like device, with the proper modifications (if necessary) of the duct(s) and/or cavities. In operation, the ejection of one or more fluid jets from one or more openings of such duct(s) or cavity may be used to move or propel or stir the device, or a part thereof, within the body cavity, or lumen, or the space within which such devices are disposed during their operation.

While the invention has been described with respect to a limited number of embodiments, it will be appreciated that many variations, modifications and other applications of the invention may be made which are within the scope and spirit of the invention.

What is claimed is:

1. An autonomous in vivo sensing device comprising:
   a sensor;
   a duct disposed substantially within the autonomous in vivo sensing device; and
   a propulsion device disposed within the duct.
2. The device of claim 1, wherein the sensor includes an imager.
3. The device of claim 1, wherein the propulsion device includes at least a propeller.
4. The device of claim 1, comprising a motor.
5. The device of claim 1, comprising a set of valves.
6. The device of claim 1, wherein the propulsion device includes a rudder.
7. The device of claim 1, comprising a receiver.
8. The device of claim 1, wherein the receiver is capable of receiving control information.
9. The device of claim 1, comprising a receiver capable of receiving power from a source external to the device.
10. The device of claim 9 wherein propulsion is provided by propelling fluid, the device comprising:
    a set of valves; and
    a controller, wherein per the control information the controller is capable of operating the set of valves to provide directional control of fluid flow.
11. The device of claim 9 comprising:
    a motor; and
    a controller capable of operating the motor.
12. The device of claim 1, comprising a power source.
13. The device of claim 1, comprising a position unit.
14. The device of claim 1, comprising a movement detection unit.
15. The device of claim 1, comprising at least one coil capable of receiving electromagnetic energy.
16. The device of claim 1, wherein the duct includes at least an inlet and an outlet.
17. The device of claim 1, wherein the duct includes a plurality of outlets.
18. The device of claim 1, wherein the device is an ingestible capsule.
19. The device of claim 1, comprising
    an internal space; and
    a stator disposed within the internal space, wherein the duct defines a space separate from the internal space, and wherein the propulsion device is disposed substantially within the duct.
20. The device of claim 1, wherein the motor includes at least a stator unit including at least one electrically conducting coil; and the propulsion device includes at least a rotor unit including at least one permanently magnetized propeller member having a north pole and a south pole.
21. An autonomous in vivo sensing device comprising:
    a sensing means for collecting data;
    a duct means for accepting and expelling fluid; and
    a propulsion means for propelling fluid, the propulsion means disposed within the duct means of said autonomous in vivo sensing device.
22. An autonomous in vivo imaging device comprising:
    an imager;
    a duct disposed substantially within the autonomous in vivo device;
    a propulsion device disposed within the duct; and
    a motor capable of operating the propulsion device.

* * * * *